United States Patent
Smith et al.

(10) Patent No.: US 7,138,442 B2
(45) Date of Patent: Nov. 21, 2006

(54) REDUCED EXOTHERMIC BONE REPLACEMENT CEMENT

(75) Inventors: Daniel B Smith, Warsaw, IN (US); Barry L Eppley, Avon, IN (US)

(73) Assignee: Biomet, Inc., Warsaw, IN (US)

( * ) Notice: Subject to any disclaimer, the term of this patent is extended or adjusted under 35 U.S.C. 154(b) by 417 days.

(21) Appl. No.: 10/232,274

(22) Filed: Aug. 30, 2002

(65) Prior Publication Data
US 2004/0044096 A1  Mar. 4, 2004

(51) Int. Cl.
*A61F 2/02* (2006.01)
*C08K 3/30* (2006.01)

(52) U.S. Cl. .................. 523/113; 523/115; 523/116; 523/218; 524/423; 424/422

(58) Field of Classification Search .............. 523/113, 523/115, 116, 218; 524/423; 424/422
See application file for complete search history.

(56) References Cited

U.S. PATENT DOCUMENTS

| | | | | |
|---|---|---|---|---|
| 3,741,926 A | * | 6/1973 | Jurecic | ........... 523/116 |
| 4,341,691 A | * | 7/1982 | Anuta | ........... 523/116 |
| 4,373,217 A | | 2/1983 | Draenert | |
| 4,718,910 A | | 1/1988 | Draenert | |
| 4,837,279 A | * | 6/1989 | Arroyo | ........... 525/193 |
| 4,843,112 A | | 6/1989 | Gerhart et al. | |
| 4,910,259 A | * | 3/1990 | Kindt-Larsen et al. | ...... 525/259 |
| 5,343,877 A | | 9/1994 | Park | |
| 5,650,108 A | | 7/1997 | Nies et al. | |
| 5,795,922 A | * | 8/1998 | Demian et al. | ........... 523/117 |

OTHER PUBLICATIONS

P. Fitzgerald, "A gamma scrintigraphic evaluation of the precorneal residence of liposomal formulations in the rabbit", J. Pharm. Phamracol. 39:487-490 (1986).
Ellis, et al., "Comparative intaocular levels of pilocarpine achieved with drops and respitory preparation", Journal Ocular Pharmacology, Summer 3(2) 121-8.
Dale meisner, et al., "Liposomal opthalmic drug delivery", International Journal of Pharmaceutics, 55,105-113 (1989).
International Search Report for PCT/US03/26353 dated Oct. 27, 2004 (3 sheets).

* cited by examiner

*Primary Examiner*—Tae H. Yoon
(74) *Attorney, Agent, or Firm*—Harness, Dickey & Pierce, P.L.C.

(57) ABSTRACT

A bone cement having a dry component including a large constituent and a small constituent. The small constituent fills a substantial volume of the interstitial spaces between the particles of the large constituent. Therefore, only a second or minor interstitial space is left remaining between the individual particles of the small constituent and the particles of the small constituent and the particles of the large constituent. Therefore, a reduced amount of a polymerizable component need be added to the dry component to form a bone cement. Such a bone cement formulation decreases the exothermic temperature of the bone cement and decreases the possibility of tissue necrosis in the implantation area.

25 Claims, 1 Drawing Sheet

REDUCED EXOTHERMIC BONE REPLACEMENT CEMENT

TECHNICAL FIELD

The present invention relates to bone replacement materials, and particularly relates to reduced exothermic bone replacement materials.

BACKGROUND

The human body includes a large structural complement including a bone structure. This bone structure, however, may become damaged or need repair for various reasons. Generally, implants may be used to replace or repair damaged portions of the bone structure. One means of fixing these replacements to the bone structure is a bone cement or bone replacement. Moreover, the bone cement itself may be used as a prosthetic material.

In one example, a bone replacement may be used to reconstruct a portion of the bone structure. For example, in a cranio-facial application, the bone replacement may be molded to reconstruct a portion of the or anatomy that has been damaged due to disease, injury, congenital defect, or surgery. Therefore, the structure supporting the muscle and skin portions of the human anatomy can be replaced using the bone replacement material. Such bone replacement materials may also be used for more orthopedic applications where the bone replacement must support a load or be load bearing portion of the anatomy.

Most moldable bone replacement materials, often referred to as bone cement, include or are formed of an acrylic. In particular, the polymer of the bone cement includes a polymethylmethylacrylate (PMMA). Most often, finely divided portions of this PMMA is provided and mixed with a liquid monomer or polymerizable material such as acrylicesters. A polymerizing initiator is then added or released into the mixture and the mixture begins to polymerize and harden. For a short period of time, during the polymerization, the entire mixture is doughy or workable so that a physician may form the material into the shape and size desired for implantation and use.

The polymerization of the liquid is an exothermic reaction. Therefore, the bone cement increases in temperature or radiates heat during the polymerization process. Generally, the temperature of bone cement may increase to such a degree as to cause tissue necrosis. The necrosis can occur if the bone cement is implanted before the bone cement cools, or if the area is not cooled, such as by irrigation. This can decrease the efficiency of forming the bone cement in situ.

It has been proposed to produce an acrylic bone cement that has a large majority of large particles to form a highly porous final material. This porous bone cement allows for a large majority of bone in-growth into the porous structure. The porous bone cements require that the bone cement be formed in such a way to produce the porous product to allow bone in-growth.

Nevertheless, it is often desired to produce a non-porous bone cement while including reduced exothermic energy. That being, a bone cement that has a high strength due to the lack of pores, while still including a cool workable period so that it may be molded in situ to achieve those advantages.

SUMMARY OF THE DISCLOSURE

A bone cement that has an exothermic energy, while it is hardening, that does not create a high or substantially necrotic temperature. The exothermic energy is produced during the polymerization of the liquid that interconnects the solid or dry particles of the bone cement. The bone cement generally includes both a powder component and a liquid component which are then mixed together. The powder component may include a large particle constituent and a small particle constituent. The small constituent has an average per particle surface area and volume that is substantially smaller than the average per particle surface area or volume of the large constituent. Therefore, the small particles can fill a substantial portion of the interstitial space between the large particles. The liquid component fills the remaining interstitial space to form a substantially solid and pore free bone cement. Due to the small surface area to volume ratio of the large particles, a reduced amount of liquid component is needed to form a bone cement, thereby reducing the amount of polymerization that must occur to form the bone cement. The reduced or limited amount of the liquid component allows the bone cement to harden without producing undo exothermic energy where substantially no or only an insignificant amount of tissue necrosis occurs.

A first embodiment provides a substantially nonporous biocompatible bone replacement formed by the combination of dry and liquid components. The bone cement includes a small particle constituent, less than 50 weight percent of a large particle constituent, and a liquid which may be polymerized. When the liquid is polymerized, it forms a polymer structure to hold the small particle constituent and the large particle constituent relative to one another.

A second embodiment provides a biocompatible bone replacement including at least 50 weight percent small particle constituent, at least 10 weight percent large particle constituent and the remainder a liquid constituent. The liquid constituent is able to polymerize after mixing with the small constituent and the large constituent. The small particle constituent, large particle constituent, and liquid constituent are able to produce an exothermic reaction energy that does not create a significant amount of necrosis of human biological tissue when mixed. The biocompatible bone replacement includes less than 5 percent pores.

A third embodiment provides a biocompatible bone replacement for implantation formed by mixing together at least 49 weight percent of a fine constituent having a first average surface area, less than 50 weight percent of a coarse constituent having a second average surface area, and the remaining portion a liquid. The liquid is able to form a polymer structure to hold the fine constituent and the coarse constituent in a selected position. The second average surface area is at least four times larger than the first average surface area.

Further areas of applicability of the present disclosure will become apparent from the detailed description provided hereinafter. It should be understood that the detailed description and specific examples, while indicating various embodiment(s), are intended for purposes of illustration only and are not intended to limit the scope of the disclosure.

BRIEF DESCRIPTION OF THE DRAWINGS

The present invention will become more fully understood from the detailed description and the accompanying drawings, wherein.

DETAILED DESCRIPTION OF THE EMBODIMENT(S)

The following description of the embodiment(s) is merely exemplary in nature and is in no way intended to limit the invention, its application, or uses.

Figure 1:
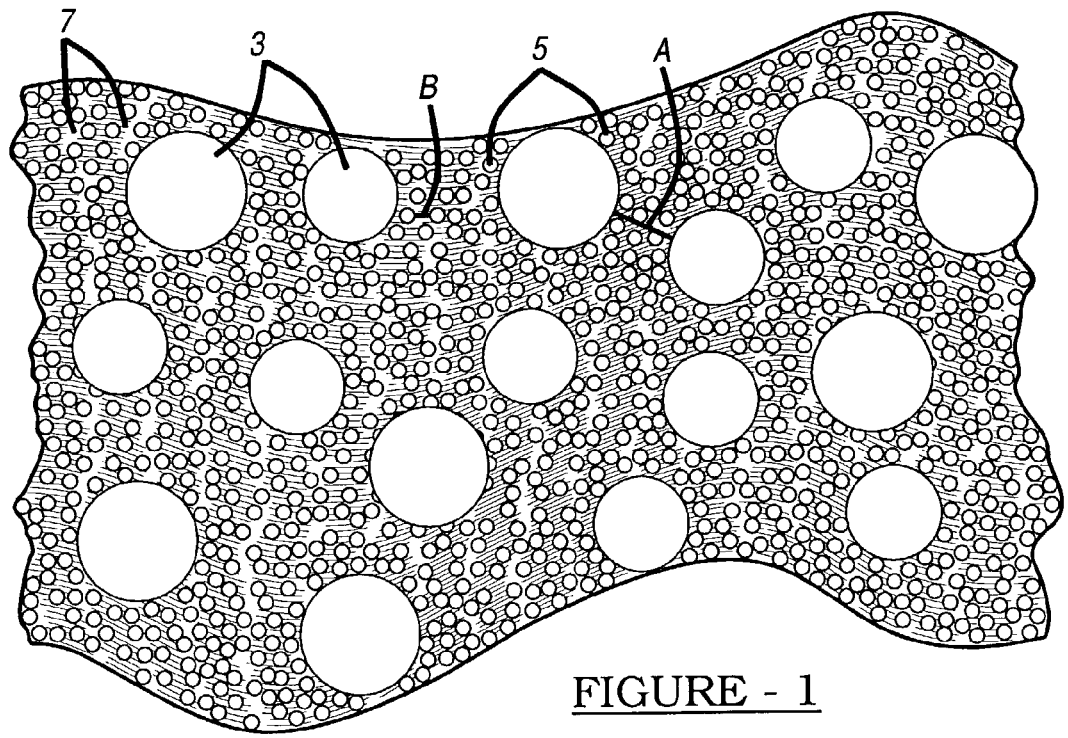
FIG. 1 is a diagrammatic cross-section of a bone cement, not to scale, according to an embodiment of the formulation disclosed herein in a doughy state.

With reference to FIG. 1, a bone cement 1 generally includes a dry component including a large particle or constituent 3 and a small particle or constituent 5. Defined between the large particles 3 are large interstitial spaces or voids A. Disposed within the large interstitial spaces A are the small particles 5. The small particles 5 fill a substantial volume of the large interstitial spaces A between the large particles 3. Defined between each of the small particles 5 and between the small particles 5 and the large particles 3 are small interstitial spaces B. A liquid 7 is then added to or mixed with the dry component to substantially fill the small interstitial spaces B. Before the bone cement 1 has hardened, it is in a slightly doughy or workable stage. At this point, the bone cement 1 may be molded to any desired shape before or after implantation.

The dry component 3 and 5 and the liquid component 7 are generally kept separate until an implantation time is at hand. Prior to the implantation of the bone cement 1, the dry component 3 and 5 and the liquid component 7 are mixed. After mixing, the two components form the doughy or workable bone cement 1. The workable bone cement 1 can be worked into any number of shapes or sizes depending upon the necessities of the implantation site or procedure. During the workable time, the dry component 3 and 5 is wetted by the liquid component 7. Also, polymerization of the liquid component 7 begins. After a period of time, the polymerization nears an end and the bone cement 1 begins to harden. Once the polymerization of the liquid component 7 is complete, the bone cement is substantially hard and non-workable. At this point, the liquid component 7 has substantially polymerized therefore producing a substantially hard and complete structure, which surrounds and includes the dry component.

Figure 2:
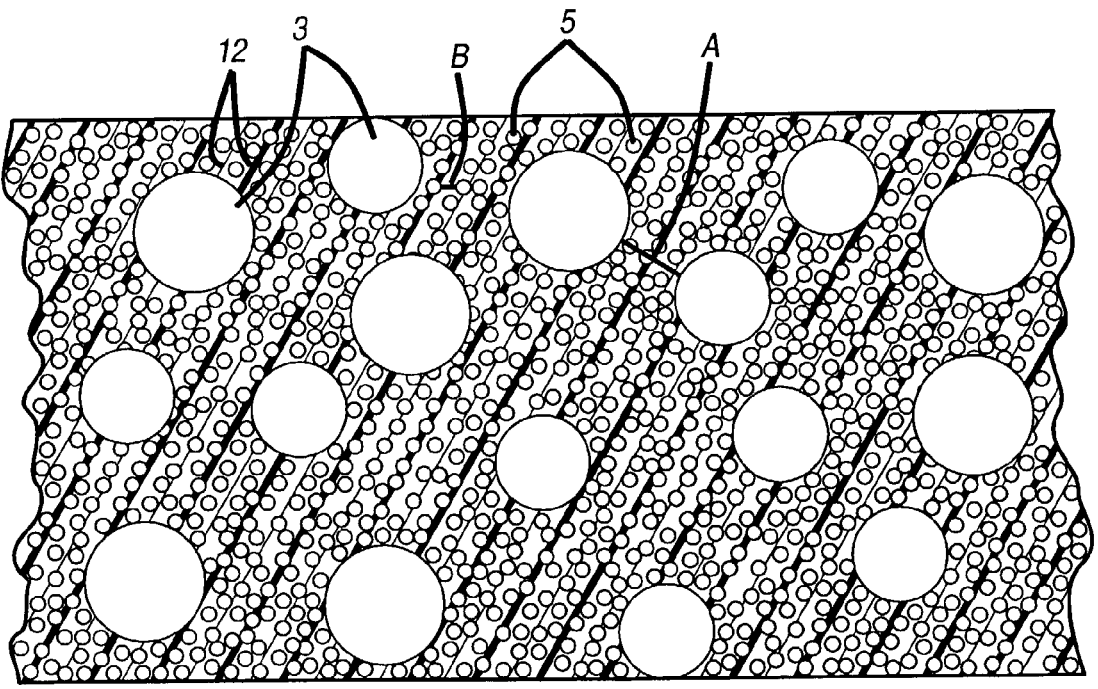
FIG. 2 is a diagrammatic cross-section of a bone cement, not to scale, according to an embodiment of the formulation disclosed herein in its hardened state.

With reference to FIG. 2, a hardened bone cement portion 10 generally includes the large constituent 3, the small constituent 5, and a polymer structure 12 formed after the polymerization of the liquid component 7. Although the illustration in FIG. 2 is merely an exemplary diagram of the hardened bone cement 10, the fine constituent 5 and the polymer structure 12 substantially fills the space between the particles of the large constituent 3 to form a substantially non-porous bone cement 10. After the hardened bone cement portion 10 is formed, the fine constituent 5 substantially fills the large interstitial spaces A between the large particles 3. The polymer structure 12, which is the hardened liquid component 7, fills the small interstitial spaces B between the individual small particles 5 and between the small particles 5 and the large particles 3. Therefore, the fine constituent 5 fills or substantially fills the area between each of the individual large particles 3, the large interstitial space A. The polymer structure 12, therefore, fills only the remaining small interstitial spaces B between the individual particles of the fine constituent 5 and between the particles of the fine constituent 5 and the large constituent 3. Because of the inclusion of the fine constituent 5, the amount of a liquid component 7 necessary to form the appropriate polymer structure 12 is reduced. The polymer structure 12 substantially fills only the areas remaining between the individual fine particles 5 and between the fine particles 5 and the large particles 3. Moreover, the hardened bone cement 10 is substantially non-porous due to the amount of fine constituent 5 and the polymer structure 12.

The dry component generally includes a divided or finely divided polymer mixture generally formed as beads of any selected geometry. The dry component according to the present formulation includes at least the large or coarse particle or constituent 3 and the small or fine particle or constituent 5. The dry component may also include other constituents such as a radiopacifier, initiator, or medicines. The initiator both initiates and is consumed in the polymerization of the liquid component 7 as it forms the polymer structure 12. Each of the dry components are held in place or held together by a polymer matrix or structure 12 formed by the polymerization of the liquid component 7.

The large constituent 3 may include both polymeric and inorganic materials. For example, the large constituent 3 may include polymer beads including PMMA. The large constituent 3 beads of PMMA may be formed in any appropriate manner, for example suspension polymerization or by comminuting large blocks of PMMA. Generally, the large constituent 3 includes a per particle size of about 200 µm to about 5000 µm. The per particle size is defined generally as the length of a line passing through the center of the particle connecting the two points furthest form each other on the exterior of the particle through the center. Moreover the large constituent 3 generally includes a volume of between about 1.5 µl to about 1200 µl. As discussed further herein, however, the size of the large constituent 3 may be selected depending upon desired properties of the doughy bone cement 1 or the hardened bone cement 10. One example includes selecting desired doughiness during the workable time and the final compressive and tensile strengths. Moreover, the large constituent 3 are generally spherical, but may also be selected depending upon desired properties of the bone cement 1, 10. The large constituents, may also be formed of inorganic materials. Suitable examples include biocompatible metals, minerals, or ceramics. Although the polymer beads may have some dissolution on the surface thereof, the relatively small amount of surface area defined by the large constituent 3 may be held in place by the polymerized liquid component 7 substantially well if the large constituent 3 is not formed of a polymer.

The fine constituent 5 may also be formed of an appropriate polymer. For example, the fine constituent 5 may be formed of a PMMA-styrene copolymer. The fine constituent 5 generally has a per particle size of about 5 µm to about 200 µm. Moreover, the fine constituent has a volume of about to 0.001 µl about 1.5 µl. As is the case with the large constituents 3, the final size and shape of the fine constituent 5 may be selected depending upon the desired properties of the bone cement 1, 10. The fine constituent 5 may also include other additives such as a radiopacifier, one example includes barium sulfate. It will be understood that although generally many additives, not including the portions which are polymerized and formed to the actual bone cement 1,10, are within the size range of the fine constituent 5, some additives may be within the size range of the large constituent 3.

The fine constituent 5 may also be formed of an appropriate polymer. For example, the fine constituent 5 may be formed of a PMMA-styrene copolymer. The fine constituent 5 generally has a per particle size of about 5 µm to about 200 µm. Moreover, the fine constituent has a volume of about 0.001 µl to about 1.5 µl. As is the case with the large constituents 3, the final size and shape of the fine constituent 5 may be selected depending upon the desired properties of the bone cement 1, 10. The fine constituent 5 may also include other additives such as a radiopacifier, one example includes barium sulfate. It will be understood that although generally many additives, not including the portions which are polymerized and formed to the actual bone cement 1,10, are within the size range of the fine constituent 5, some additives may be within the size range of the large constituent 3.

The monomer of the liquid component 7 is polymerized with a polymer initiator to form the polymer matrix 12 which holds the dry component in place. Together the two components form the bone cement 10 which may be implanted into a patient at a desired location. The liquid component 7, may be formed of other materials that are able to polymerize in the form the desired structure to produce a desirable bone cement.

As a broad overview of forming a bone cement 1, 10 and for clarity of the description, the following is provided. The dry component and liquid component 7 are generally kept separate prior to being mixed for implantation. As the dry component and liquid component 7 are mixed, the liquid component 7 wets the dry component. The liquid component 7 then begins to polymerize and form a solid polymer structure 12 that holds the dry component in place. If the dry component is formed of an appropriate polymer, a small portion of the surface area of the dry component may also dissolve and be polymerized with the liquid component 7 thereby forming a more intimate and strong interaction. Nevertheless, such a direct polymerization is not required to form the hardened bone cement 10.

As the polymerization occurs, being an exothermic reaction, the bone cement 1 begins to increase in temperature. Simply the polymerization is an exothermic reaction which produces a temperature increase of the bone cement 1. The heat is in direct proportion to the amount of polymerization occurring. Therefore, a reduction in the total amount of the liquid component 7 reduces the total amount of exothermic energy produced as the liquid component 7 polymerizes. Simply, the less material polymerizing and producing heat, the less heat that is produced. Therefore, including a smaller absolute surface area or volume which must be coated or filled by the liquid component 7, the less liquid component 7 required to form the appropriate bone cement 1, 10. Moreover, the inclusion of the small constituent 5 substantially reduces the amount of the liquid component 7 required to form the solid and substantially non-porous bone cement 10. If only the large constituent 3 were used in the dry component, the volume of the resulting interstitial spaces would be substantially greater than when the small constituent 5 is used to fill a substantial volume of the interstitial spaces between the large constituent 3. Therefore, including the small constituent 5 reduces the amount of the liquid component 7 required to form the appropriate polymer structure 12 to form the substantially non-porous and hardened bone cement 10.

The dry component may generally include about 50 to about 90 weight percent small constituent 5 and the remainder large constituent 3. The overall volume of dry component is equivalent to previously known bone cement formulations, but may be changed depending upon the application. Including the large constituent 3 reduces the total surface area of the volume of dry component that is required to be covered by the liquid component 7 to form the polymeric matrix. It will be understood that the entire surface generally includes the combination of the surface area of the total amount of large constituents 3 and small constituents 5. As mentioned above, the small constituent 5 also fills a substantial majority of the volume between the large constituents 3. Therefore, a second theory of the formulation of the bone cement 10 is that including the small constituent 5 reduces the volume of the liquid component 7 required to fill the interstitial spaces of the dry component to form the hardened bone cement 10. Due to the reduced volume of the liquid component 7 required, the per volume exothermic energy of the workable bone cement 1 as it polymerizes to form the hardened bone cement 10 is reduced, and thus the temperature generated by the exothermic reaction is reduced. The polymerization of the liquid component 7 produces the exothermic energy per unit, therefore reducing the units of the liquid component used reduces the amount of exothermic energy produced.

The bone cement 1, 10 precursors include both the dry component and the liquid component 7. Therefore, as a weight percent of the mixed bone cement, the small constituent 5 is generally about 20 weight percent to about 80 weight percent of the bone cement precursor. The large constituent 3 is generally about 18 weight percent to about 49 weight percent of the bone cement precursor. Finally, the liquid component 7 is generally between about 5 weight percent to about 50 weight percent of the bone cement precursor. Each of these materials are mixed in appropriate proportions to form the bone cement 1, 10. Although it will be understood, as mentioned above, the specific ratios may be modified depending upon the desired qualities of the resultant bone cement 1, 10 during its different phases. The qualities include polymerization time and workability properties and time.

Including the small constituent 5 reduces the volume of the interstitial spaces between dry components, thereby reducing the amount of the liquid component 7 required to form the bone cement 1, 10. The inclusion of an appropriate amount of the fine constituent 5 and the liquid component 7 form a substantially non-porous hardened bone cement 10. Although the bone cement 10 may have a higher porosity by including less of the fine constituent 5 and less of the liquid component 7, the substantially non-porous bone cement 10 results by filling the pores or voids between the large constituent 3 with the small constituent 5 and liquid component 7. The non-porous bone cement 10 generally has a strength which is higher than a porous bone cement of the same volume. Therefore, including at least 20 weight percent fine constituent and enough of the liquid component 7, to form the bone cement 10, produces the bone cement 10 which is substantially non-porous or less than about 5% porous. This porosity may be isolated or interconnecting. Nevertheless, porosity is generally substantially limited.

An exemplary way to form the bone cement, and to reduce porosity further, is to form it in a vacuum sealed package. Appropriate packages are disclosed in U.S. Pat. No. 5,370,221 entitled "Flexible Package For Bone Cement Components" and U.S. Pat. No. 5,398,483, entitled, "Method and Apparatus for Packaging, Mixing, and Delivering Bone Cement," both incorporated herein by reference. The package allows the components of the bone cement to be mixed together under a vacuum. While being mixed in the vacuum, extraneous gases are removed from the bone cement mixture as it is being mixed and the liquid component begins to polymerize. Generally, the dry component is kept separate from the liquid component 7 in a single pouch using a removable seal or clamp. The clamp is removed from the package when the two components are desired to be mixed to form the bone cement. Generally, the portion of the package which includes the dry component has been vacuum sealed such that there is substantially no gases in the interstitial spaces between the individual particles. Moreover, there is a terminal area, having a vacuum formed therein, in gaseous communication with the portion of the package including the dry components wherein when the liquid component 7 is forced into the dry component any further gases are pulled into the terminal area. Therefore, substantially any gases in the interstitial spaces of the dry component are removed during the mixing process substantially removing any gaps between the particles. These factors help decrease the porosity of the final bone cement product 10. Therefore, using a mixing package to form the bone cement 10, may produce a bone cement 10 which is substantially highly non-porous or has a porosity below about 1%.

EXAMPLE 1

Bone Cement Precursor Formulation

An exemplary bone cement formulation includes a dry component and a liquid component. The dry component includes 60% PMMA-styrene copolymer beads (fine constituent), 10% barium sulfate (fine constituent), and 30% PMMA polymer beads (large constituent). The PMMA-styrene copolymer has an average particle size of about 65 micrometers. The PMMA polymer has an average particle size of about 750 micrometers. The liquid component of the formulation includes about 98% MMA monomer, about 2% dimethyl-p-toluidine, and about 60 PPM hydroquinone. The liquid component has a density of 0.94 grams per milliliter.

EXAMPLE 2

Bone Cement Formation

Approximately 40 grams of the dry component from Example 1 is mixed with about 14.5 milliliters of the liquid component from Example 1. The mixture is then mixed by hand and allowed to polymerize. The maximum exothermic temperature recorded of the mixture per the ASTM 451 method is about 52° C. (about 120° F.). The mixture reaches its dough or workability stage at about three minutes after the start of mixing. The mixture sets to its final polymerized state at about 9 minutes at about 23° C. ambient temperature.

Therefore the bone cement 10, using the components disclosed herein, forms a substantially non-porous bone cement 10. That being the bone cement 10 formed generally includes a porosity less than about 5% and may be formed in a package or device to have a porosity of less than about 1%. The general lack of porosity is provided by the fact that there is enough of the fine constituent 5 and liquid component 7 to substantially close or fill any pores that may be formed due to the large constituent 7. The fine constituent 5 and liquid component 7 fill the interstitial spaces between the large constituent 3 particles. Moreover, the bone cement 10, which has a high compressive strength and substantially non-porous structure, can be formed without producing a high exothermic temperature. Therefore, the bone cement 10 can be used in sensitive areas and need not be internally irrigated or cooled to stop tissue necrosis. In addition, surgical areas may be closed before the bone cement has fully polymerized or set thereby decreasing the surgical time required when using the bone cement.

One exemplary use of the bone cement 1, 10 is for cranio-facial bone reconstruction. One place that is exceptionally delicate includes cranial reconstruction where the bone cement may contact the dura mata. Therefore, bone necrosis or other tissue necrosis can be a substantial problem in these sensitive areas due to the fine or thin outer tissues and the fine bone structure. In these areas, it is desirable to use a substantially non-exothermic or low exothermic material for bone reconstruction in these areas. It is also highly desirable to place a workable bone cement in a surgical site for reconstructive surgery so that the formation or working of the bone cement can be done in situ to produce the most aesthetically pleasing results.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A substantially nonporous biocompatible material formed by the combination of constituents, comprising:
   a small particle constituent of a bone replacement forming polymer or co-polymer material;
   about ten weight percent but less than 50 weight percent of a large particle constituent of the biocompatible material;
   a liquid adapted to be polymerized to form the bone replacement;
   wherein the polymerized liquid forms a polymer structure to hold said small particle constituent and said large particle constituent relative one another,
   wherein said large particle constituent includes an average particle size of at least 500 μm.

2. The substantially nonporous biocompatible of claim 1, wherein said large particle constituent forms about 10 weight percent to about 30 weight percent of the bone replacement; and wherein said liquid constituent forms about 10 weight percent to about 30 weight percent of the bone replacement.

3. The substantially nonporous biocompatible of claim 1, wherein said small particle constituent and said large particle constituent are formed of a material selected from polymers or copolymers of methyl methacrylate, methylacrylate, styrene, or other esters of methacrylic acid.

4. The substantially nonporous biocompatible of claim 1, wherein said liquid component includes a monomer, polymerization accelerator, stabilizer, or mixtures thereof, wherein when said liquid component is mixed with said large particle constituent and said small particle constituent said monomer polymerizes to form the polymer structure.

5. A substantially nonporous biocompatible bone replacement formed by the combination of constituents, comprising:
   a small particle constituent of a bone replacement forming polymer or co-polymer material;
   about ten weight percent but less than 50 weight percent of a large particle constituent of a bone replacement wherein the particle size of the large particular constituent is at least 500 microns;
   a liquid adapted to be polymerized to form the bone replacement;
   wherein the polymerized liquid forms a polymer structure to hold said small particle constituent and said large particle constituent relative one another,
   wherein said small particle constituent form about 50 weight percent of the bone replacement.

6. A biocompatible bone replacement, comprising:
   at least 50 weight percent of a small particle constituent;
   at least 10 weight percent of a large particle constituent having a particle size of at least 500 microns, wherein said weight percent of small particle constituent is greater than the weight percent of the large particle constituent; and the remainder a liquid constituent that is able to polymerize after mixing with said small constituent and said large constituent;

wherein said small particle constituent and said large particle constituent, are provided so that said liquid constituent is able to be mixed to create an exothermic reaction energy that does not create a significant amount of necrosis of human biological tissue;

wherein the biocompatible bone replacement includes less than 5 percent pores.

7. The biocompatible bone replacement of claim 6, wherein said liquid component includes a polymerizable compound, a polymerization accelerator, stabilizer, or mixtures thereof, wherein when said liquid component is mixed with said large particle constituent and said small particle constituent said polymerizable compound polymerizes to form a polymer structure.

8. The biocompatible bone replacement of claim 7, wherein when the polymer structure is being formed the bone replacement does not increase in temperature above about 52° C. as measured by ASTM F451.

9. The biocompatible bone replacement of claim 6, wherein said small particle constituent includes an average particle size of about 5 µm to about 200 µm.

10. The biocompatible bone replacement of claim 6, wherein said large particle constituent forms about 20 weight percent to about 30 weight percent of the bone replacement; and wherein said liquid constituent forms about 20 weight percent to about 30 weight percent of the bone replacement.

11. A biocompatible bone replacement, comprising:
at least 50 weight percent small particle constituent;
at least 10 weight percent large particle constituent having an average particle size of at least 500 µm, wherein said weight percent of small particle constituent is greater than the weight percent of the large particle constituent; and
the remainder a liquid constituent that is able to polymerize after mixing with said small constituent and said large constituent;
wherein said small particle constituent and said large particle constituent, are provided so that said liquid constituent is able to be mixed to create an exothermic reaction energy that does not create a significant amount of necrosis of human biological tissue;
wherein the biocompatible bone replacement includes less than 5 percent pores;
wherein said large particle constituent is formed of a material selected from polymers or copolymers of methylmethylacrylate, methylacrylate, styrene, or other esters of methacrylic acid.

12. The biocompatible bone replacement of claim 6, wherein said small particle constituent includes methylmethylacrylate.

13. A biocompatible bone replacement for implantation, comprising mixing constituents together including;
at least 49 weight percent of a fine constituent having a first maintained average surface area;
less than 50 weight percent of a coarse constituent having a second maintained average surface area and an average particle size of at least 500 µm; and
the remaining portion a liquid to form a polymer structure to hold said fine constituent and said coarse constituent in a selected position upon polymerization of said liquid;
wherein said second maintained average surface area is at least four times larger than said first maintained average surface area;
wherein at least a portion of said fine constituent and a portion of said coarse constituent is cross-linkable with said liquid.

14. The biocompatible bone replacement of claim 13, wherein said coarse constituent forms about 10 weight percent to about 30 weight percent of the bone replacement; wherein said liquid forms about 10 weight percent to about 30 weight percent of the bone replacement; and wherein said fine constituent is about 50 weight percent to about 80 weight percent.

15. The biocompatible bone replacement of claim 13, wherein said liquid component includes a monomer, a polymerization accelerator, stabilizer, or mixtures thereof, wherein when said liquid is mixed with said coarse constituent and said fine constituent said monomer polymerizes to form the polymer structure.

16. The biocompatible bone replacement of claim 13, wherein said fine constituent and said coarse constituent substantially define spheres.

17. The biocompatible bone replacement of claim 13, wherein when the polymer structure is formed, the bone replacement is less than 5 percent porous.

18. A substantially nonporous biocompatible bone replacement formed by mixing portions comprising:
a small particle portion, wherein each small particle has a volume less than 1.5 µl;
less than 50 weight percent of a large particle portion, wherein each large particle has an average particle size of at least 500 µm; and
a liquid portion that polymerizes to hold said small particle portion and said large particle portion relative to each other.

19. The substantially nonporous biocompatible bone replacement of claim 18, wherein said large particle constituent forms about 10 weight percent to about 30 weight percent of the bone replacement; and wherein said liquid constituent forms about 10 weight percent to about 30 weight percent of the bone replacement.

20. The substantially nonporous biocompatible bone replacement of claim 18, wherein said liquid component includes a monomer that polymerizes to form a polymer structure.

21. A biocompatible bone replacement, comprising:
at least 50 weight percent of a small particle constituent;
a large particle constituent having an average size of at least 500 µm constituting about 10 weight percent but less than about 30 weight percent of the biocompatible bone replacement; and
the remainder a liquid constituent that is able to polymerize after mixing with said small constituent and said large constituent;
wherein the remainder weight percent of the liquid constituent does not raise the temperature of the implanted biocompatible bone replacement to create a significant amount of necrosis of human biological tissue during polymerization of the liquid constituent.

22. The biocompatible bone replacement of claim 6, wherein the biocompatible bone replacement includes less than 5 percent pores.

23. A biocompatible bone replacement formed by the combination of constituents, comprising:
   at least 50 weight percent of the bone replacement a small particle constituent of a bone replacement having a particle size of less than 175 microns;
   at least ten weight percent of a large particle constituent of a bone replacement having a particle size of at least 500 microns; and
   a monomer liquid polymerizable relative to the small particle constituent and the large particle constituent to form the bone replacement;
   wherein the polymerized liquid forms a polymer structure to hold said small particle constituent and said large particle constituent relative one another.

24. The substantially nonporous biocompatible of claim 1, wherein when the polymer structure is being formed the bone replacement does not increase in temperature above 60° C. as measured according to ASTM F451.

25. The biocompatible bone replacement of claim 13, wherein when the polymer structure is being formed the bone replacement does not increase in temperature above 65° C. as measured by ASTM F451.

* * * * *